United States Patent [19]

Newman et al.

[11] 4,424,806

[45] Jan. 10, 1984

[54] AUTOMATED VENTILATION, CPR, AND CIRCULATORY ASSISTANCE APPARATUS

[75] Inventors: Bill H. Newman, Bothell; Clifton A. Alferness, Woodinville, both of Wash.

[73] Assignee: Physio-Control Corporation, Redmond, Wash.

[21] Appl. No.: 243,196

[22] Filed: Mar. 12, 1981

[51] Int. Cl.³ ............................................ A61M 16/00
[52] U.S. Cl. .................................. 128/28; 128/205.25
[58] Field of Search .................. 128/28, 30, 30.2, 134, 128/298, 299, 205.25, 205.26, 201.27, 201.28

[56] References Cited

U.S. PATENT DOCUMENTS

| | | |
|---|---|---|
| Re. 26,511 | 12/1968 | Hewson . |
| 594,961 | 12/1897 | McLean et al. . |
| 635,801 | 10/1899 | McLean . |
| 726,791 | 4/1903 | Armbruster . |
| 1,147,560 | 7/1915 | Shurtleff ............................ 128/299 |
| 1,172,660 | 2/1916 | Armbruster . |
| 1,608,239 | 11/1926 | Rosett . |
| 1,670,301 | 5/1928 | Eisenmenger . |
| 2,694,395 | 11/1954 | Brown . |
| 2,699,163 | 1/1955 | Engström ........................ 128/30.2 |
| 2,893,382 | 7/1959 | Demeny . |
| 3,078,842 | 2/1963 | Gray . |
| 3,254,645 | 6/1966 | Rand et al. . |
| 3,307,541 | 3/1967 | Hewson . |
| 3,348,536 | 10/1967 | Tambascia . |
| 3,351,052 | 11/1967 | Hewson . |
| 3,454,000 | 7/1969 | Bird et al. ............................. 128/28 |
| 3,461,860 | 8/1969 | Barkalow . |
| 3,461,861 | 8/1969 | Barkalow et al. . |
| 3,481,327 | 12/1969 | Drennen .......................... 128/30.2 |
| 3,509,899 | 5/1970 | Hewson . |
| 3,511,275 | 5/1970 | Hewson . |
| 3,552,390 | 1/1971 | Muller . |
| 3,610,237 | 10/1971 | Barkalow et al. . |
| 3,659,593 | 5/1972 | Vail . |
| 3,662,751 | 5/1972 | Barkalow et al. . |
| 3,713,446 | 1/1973 | Sarnoff . |
| 3,835,845 | 9/1974 | Maher . |
| 3,865,103 | 2/1975 | Folman . |
| 3,866,604 | 2/1975 | Curless et al. . |
| 3,878,839 | 4/1975 | Norton et al. . |
| 3,880,149 | 4/1975 | Kawaguchi . |
| 3,896,797 | 7/1975 | Bucur . |
| 3,961,626 | 6/1976 | Honchen et al. ............... 128/201.27 |
| 4,057,046 | 11/1977 | Kawaguchi . |
| 4,060,079 | 11/1977 | Reinhold, Jr. . |
| 4,077,402 | 3/1978 | Benjamin, Jr. et al. . |
| 4,198,963 | 4/1980 | Barkalow et al. . |
| 4,349,015 | 9/1982 | Alferness ............................. 128/28 |

OTHER PUBLICATIONS

Wilder et al., "Methods of Coordinating Ventilation and Closed Chest Cardiac Massage in the Dog", Surgery, v. 53, No. 2, pp. 186-194 (1963).

Tsitlik et al., "Instrumentation for Cardiopulmonary Resuscitation", 8th Annual Northeast Bioengineering Conference, pp. 275-278 (3/27/80).

Chandra et al., "Augmentation of Carotid Flow During Cardiopulmonary Resuscitation (CPR) . . . ", The American Journal of Cardiology, v. 43, p. 422 (1979).

Rabson et al., "The Use of a Pneumatic Vest to Generate Carotid Flow in a Canine Mode of Circulatory Arrest", Circulation, v. 59 & 60, Supplement II, p. II--196 (1979).

Chandra et al., "Abdominal Binding During CPR in Man", Circulation, v. 59 & 60, Supplement II, p. II-45 (1979).

Chandra et al., "Simultaneous Chest Compression and Ventilation at High Airway Pressure During Cardiopulmonary . . . ", Circulation, v. 58, Supplement II, p. II-203 (1978).

Rudikoff et al., "Mechanisms of Blood Flow During Cardiopulmonary Resuscitation", Circulation, v. 61, No. 2, pp. 345-352 (1980).

Primary Examiner—Henry J. Recla
Attorney, Agent, or Firm—Christensen, O'Connor, Johnson & Kindness

[57] ABSTRACT

An automated ventilation, CPR and circulatory assistance apparatus includes an airway apparatus 10, a vest 12 including an inflatable bladder 18, and an abdominal restraint 14 including an inflatable bladder 22. An airway pneumatic control apparatus 84, a vest pneumatic control apparatus 86, and an abdominal restraint pneumatic control apparatus 88 are in fluid communication

4,424,806

Page 2 with the airway apparatus, the vest bladder, and the abdominal restraint bladder, respectively, and responsive to respective first and second states in an airway control signal AWC, a vest control signal VC, and an abdominal restraint control signal ARC to alternately inflate and deflate the patient's lungs, the vest bladder, and the abdominal restraint bladder, respectively. Provision is made for selectively adjusting the volume of gas that is coupled to the patient's lungs, and the maximum pressures that are obtained in the vest bladder and the abdominal restraint bladder. An electronic control means (FIGS. 5 and 6) permits selection of ventilation, CPR and circulatory assistance modes of operation, and is adapted to control lung, vest bladder and abdominal restraint bladder inflation and deflation during each mode by selectively controlling the respective times of the first and second states in each of the airway, vest and abdominal restraint control signals.

42 Claims, 9 Drawing Figures

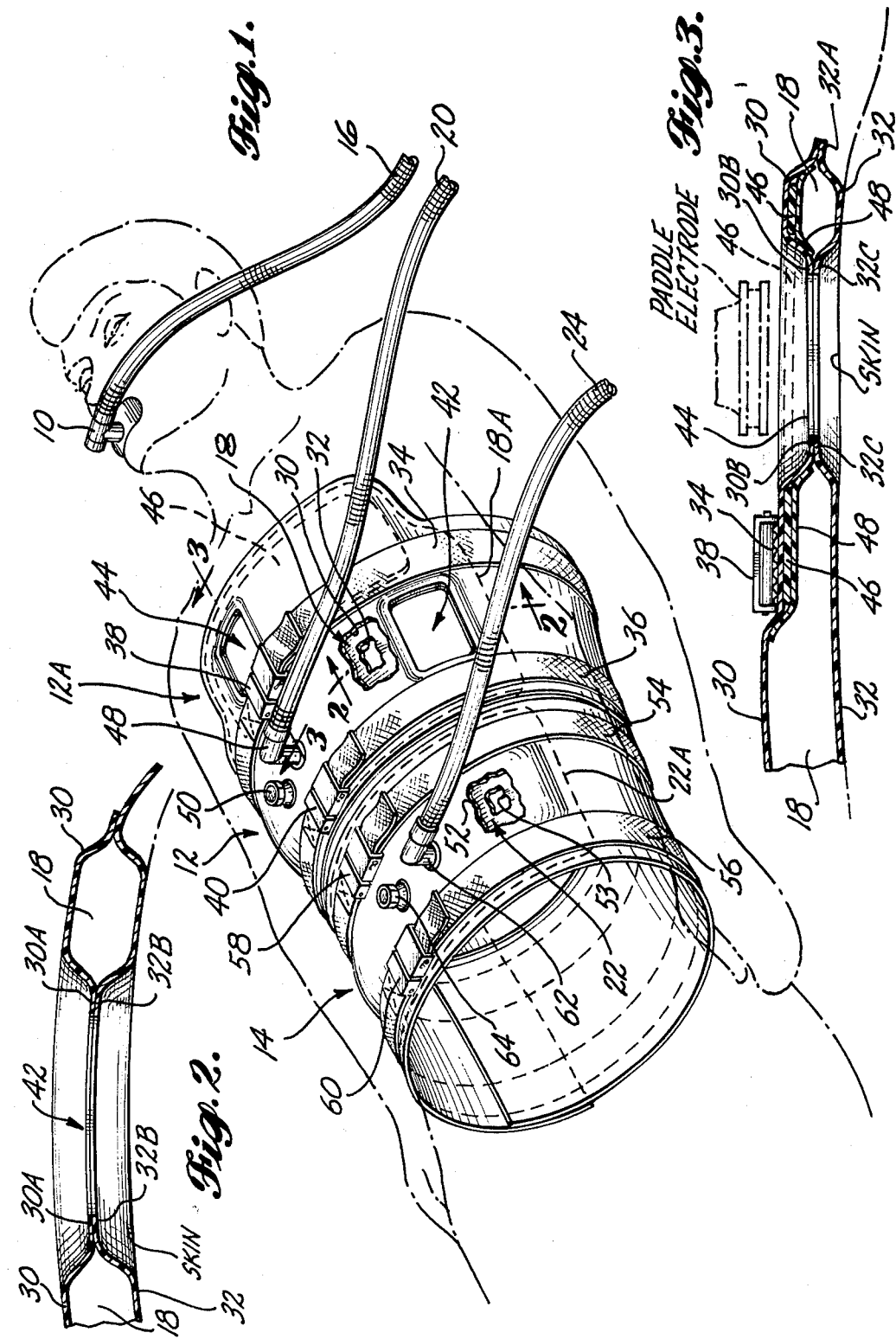

AUTOMATED VENTILATION, CPR, AND CIRCULATORY ASSISTANCE APPARATUS

FIELD OF THE INVENTION

This invention generally relates to apparatus for assisting or reproducing the pulmonary and cardiac functions of a patient, and, more particularly, to such an apparatus which can be selectively controlled to automatically ventilate the lungs of the patient, or to automatically effect cardiopulmonary resuscitation (CPR) of the patient, or to automatically provide circulatory assistance to the patient.

BACKGROUND OF THE INVENTION

There are a number of commonly-encountered situations in which the pulmonary and cardiac functions of a patient are impaired or absent, thereby necessitating corrective action if the patient's life is to be maintained.

In one such life-threatening situation, the patient's cardiac function is substantially normal but the patient either is not breathing or is having difficulty in breathing, i.e., the patient's pulmonary function is either absent or substantially impaired. The appropriate corrective action normally taken is to reproduce the patient's pulmonary function by manual or automated ventilation of the patient's lungs.

In manual ventilation, a person first clears the patient's airway (e.g., the mouth, larynx, and the trachea) by removing any obstructions therein and by tilting the patient's head back and by elevating the patient's chin. After the airway has been cleared, the person reproduces the pulmonary function by either breathing into or discharging a bag respirator into the patient's mouth at a predetermined rate, e.g., twelve times per minute, to periodically inflate (and deflate) the patient's lungs through the airway. The primary disadvantage of manual ventilation is that the technique is relatively inefficient in reproducing the pulmonary function, inasmuch as only a small percentage of the normal oxygenation of the patient's blood through lung inflation is obtained. Yet another disadvantage results from the fact that a person trained in the technique must be readily available to provide manual ventilation.

To overcome the noted disadvantages of manual ventilation, ventilators have been developed that provide automated ventilation. Typically, such ventilators include a source of pressurized gas containing or consisting of oxygen, an airway apparatus that is adapted to be inserted into the patient's airway, and a control apparatus including appropriate valves for coupling the airway apparatus alternately to the source of pressurized gas and to the atmosphere so as to alternately inflate and deflate the patient's lungs. The control apparatus may be designed so as to selectively vary not only the rate at which the patient's lungs are inflated but also the characteristics of lung inflation and deflation, e.g., the maximum gas pressure that is applied to the lungs during inflation, the maximum volume of gas that is introduced into the lungs during inflation, the rate of pressure increase and decrease, and the relative durations of each alternate inflation and deflation.

In another life-threatening situation, the patient's pulmonary and cardiac functions are both absent. The appropriate corrective action normally taken is the use of cardiopulmonary resuscitation (CPR) which involves ventilation of the patient's lungs to reproduce the pulmonary function and concurrent compression of the patient's chest to reproduce the cardiac function. CPR may be effected either by a manual technique or by use of an automated CPR apparatus.

A typical manual CPR technique that is designed for use by a single person comprises the following steps. The person first clears the patient's airway, in the manner previously described, and then reproduces the pulmonary function by either breathing into or discharging a bag respirator into the patient's mouth to inflate the patient's lungs through the airway. The person then reproduces the cardiac function by compressing the patient's chest immediately above the sternum at a predetermined rate, e.g., sixty compressions per minute, in order to compress the patient's heart so as to force blood through the patient's circulatory system. Since a single person cannot both compress the patient's chest and ventilate the patient at the same time, the technique involves repetitive cycles of a predetermined number of chest compressions, e.g., fifteen, followed by a predetermined number of ventilations, e.g., two.

Although manual CPR techniques have saved countless lives, they are subject to the disadvantage that they must be used by a person who has been trained in these techniques. In order to have any chance of restoring the patient to normal health, CPR must be started within a certain period of time after the patient has been stricken. Accordingly, if a trained person is not readily available, the patient will most likely die. Another disadvantage of manual CPR techniques is that they are relatively inefficient in reproducing the cardiac and pulmonary functions. For example, manual CPR techniques can at best result in only a small percentage of the normal blood flow to the patient's brain and only a small percentage of the normal oxygenation of the patient's blood through lung inflation.

The efficiency of CPR may be increased by the use of automated CPR apparatus, sometimes referred to as resuscitators. Although the structure and operation of resuscitators differ, they typically include a ventilator similar to that previously described and a reciprocable chest plunger that is positioned by an appropriate mounting frame above the patient's chest or that is secured to the patient's chest by a plurality of straps. A control apparatus is provided which causes the reciprocable chest plunger to be extended to and from the patient's chest so as to alternately compress and decompress the patient's chest and which causes the airway apparatus of the ventilator to be alternately coupled to a source of pressurized gas and to the atmosphere. Typically, a resuscitator is operated in a cyclical mode, each cycle including a plurality of successive chest compressions and decompressions (e.g., five) followed by a single lung inflation and deflation.

The resuscitators known to the prior art are bulky and heavy, and therefore not easily transportable. The manner in which CPR is effected by such resuscitators, e.g., the rates of chest compression and decompression and of lung inflation and deflation relative to each other, the relative numbers of chest compressions and decompressions and of lung inflations and deflations during each cycle, and the duration and amount of chest compressions and of lung inflations relative to each other, is rather inflexible so that it is difficult to tailor CPR to the specific needs of the patient. Further, the reciprocable chest plunger is capable of causing significant injury to the patient.

In yet another, life-threatening situation, the patient's pulmonary function is substantially normal but the cardiac function of the patient is impaired. The appropriate corrective action normally taken is to apply drugs to the patient or to provide circulatory assistance to the patient by the use of a apparatus such as an intra-aortic balloon which is surgically inserted into the aorta through the patient's arterial system and which is inflated and deflated at a rate that is synchronized to the electrical heart activity of the patient. As can be appreciated, a trained person is required to properly apply drugs to the patient and a trained physician is required to use an apparatus such as an intra-aortic baloon.

Apparatus of the types previously described are also disadvantageous in that they are designed for use in a specific life-theatening situation, e.g., for ventilation, or for CPR, or for circulatory assistance. Since a specific life-threatening situation cannot be known in advance, it is therefore necessary to maintain on hand each type of apparatus.

Recently, it has been discovered that the mechanism for causing blood to flow through the circulatory system during CPR may not be the force that is transmitted to the heart through the chest during each chest compression, but rather the amount of intrathoracic pressure that is generated as a result of chest compression (and lung inflation) in that portion of the thorax in which the heart and lungs are located. It therefore has been postulated that an increase in intrathoracic pressure during CPR should increase the efficiency of CPR. Reference, for example, Rudikoff et al., Mechanisms of Blood Flow During Cardiopulmonary Resuscitation, CIRCULATION, v. 61, No. 2, pp. 345-352 (1980). However, there are no commercially-available automated apparatus which utilize this discovery to accordingly increase the intrathoracic pressure of the patient during CPR (and during circulatory assistance).

It is therefore an object of this invention to provide an apparatus which can be selectively controlled to automatically ventilate the lungs of a patient, or to automatically effect cardiopulmonary resuscitation, or to automatically provide circulatory assistance to the patient.

It is another object of this invention to provide such an apparatus which provides CPR and circulatory assistance by increasing the intrathoracic pressure of the patient.

It is yet another object of this invention to provide such an apparatus which is small in size and light in weight, and therefore easily transportable.

It is a further object of this invention to provide such an apparatus which is capable of flexibly controlling the manner in which ventilation, CPR and circulatory assistance are effected.

It is yet a further object of this invention to provide such an apparatus which provides more efficient CPR and more efficient circulatory assistance than currently-available apparatus and techniques.

SUMMARY OF THE INVENTION

The foregoing objects, and other objects and advantages that will be apparent to those of ordinary skill in the art, are achieved in an apparatus for assisting and reproducing the pulmonary and cardiac functions of a patient. The apparatus comprises:

an airway apparatus constructed so as to be placed during use in proximity to the patient's airway to provide fluid communication with the patient's lungs;

a vest constructed so as to be secured during use about the portion of the patient's body in the region of the thorax, the vest including an inflatable bladder that overlies the patient's chest;

an abdominal restraint constructed so as to be secured during use about the portion of the patient's body immediately below the thorax, the abdominal restraint including an inflatable bladder that overlies the patient's abdomen; and control means that is in fluid communication with the airway apparatus, the vest bladder and the abdominal restraint bladder, the control means being operable to selectively inflate and deflate the patient's lungs through the airway apparatus, and to selectively inflate and deflate the vest bladder, and to selectively inflate and deflate the abdominal restraint bladder.

Preferably, the control means includes means for selecting a ventilation mode of operation, a CPR mode of operation and a circulatory assistance mode of operation.

When the ventilation mode has been selected, the control means is operative to deflate the vest bladder and the abdominal restraint bladder, and to alternately inflate and deflate the patient's lungs through the airway apparatus at a predetermined ventilation rate.

When the CPR mode has been selected, the control means is operative to alternately inflate and deflate the patient's lungs through the airway apparatus and to alternately inflate and deflate the vest bladder in substantial synchronism with each other at a predetermined CPR rate. The abdominal restraint bladder may be either inflated, or deflated, or alternately inflated and deflated in substantial synchronism with the patient's lungs and the vest bladder at the predetermined CPR rate.

When the circulatory assistance mode has been selected, the control means is operative to alternately inflate and deflate the patient's lungs through the airway apparatus at the ventilation rate, and to alternately inflate and deflate the vest bladder at a circulatory assistance rate related to the measured heart rate of the patient. The abdominal restraint bladder may be either inflated, or deflated, or alternately inflated and deflated in substantial synchronism with the vest bladder at the circulatory assistance rate.

Preferably, such a control means: is adapted to inflate the patient's lungs with a predetermined volume of gas, and includes means for selectively adjusting such predetermined volume; is operative to inflate the vest bladder to a predetermined pressure value and includes means for selectively adjusting such predetermined pressure value; is operative to inflate the abdominal restraint bladder to a predetermined pressure value and includes means for selectively adjusting such predetermined pressure value; includes means for selectively and individually adjusting the predetermined ventilation rate and the predetermined CPR rate; includes means for selectively and individually adjusting the duty-cycles of alternate lung, vest bladder and abdominal restraint bladder inflation and deflation; includes means for selectively adjusting the relative phasing of lung, vest bladder and abdominal restraint bladder inflation and deflation when the CPR mode has been selected; and, includes means for selectively adjusting the relative phasing of vest bladder and abdominal restraint bladder inflation and deflation when the circulatory assistance mode has been selected.

The vest comprises:

a first sheet composed of a flexible, air-impermeable, nonextensible and washable material, the first sheet having a width greater than the circumference of the patient's body in the region of the thorax and having a height generally corresponding to the height of the thorax;

a second sheet composed of a flexible, air-impermeable and washable material, the second sheet having a width and height generally corresponding to the width and height of the thorax, with the periphery of the second sheet being sealed to the first sheet so as to define the inflatable vest bladder therebetween;

a fluid connector secured to the first sheet and located so as to provide a fluid flow path to and from the vest bladder; and, means affixed to the first sheet for securing the vest about the patient's body.

The abdominal restraint is similarly constructed, with the first sheet having a width greater than the circumference of the patient's body in the region immediately below the thorax and having a height generally corresponding to the height of the abdomen, and with the second sheet having a width and a height generally corresponding to the width and height of the abdomen.

BRIEF DESCRIPTION OF THE DRAWINGS

The invention can best be understood by reference to the following portion of the specification, taken in conjunction with the accompanying drawings in which:

FIG. 1 is a pictorial illustration of a preferred embodiment of the apparatus including an airway apparatus, a vest, and an abdominal restraint;

FIG. 2 is a first cross-sectional view of the vest taken along lines 2—2 in FIG. 1;

FIG. 3 is a second cross-sectional view of the vest taken along the lines 3—3 in FIG. 1;

DESCRIPTION OF THE PREFERRED EMBODIMENT

Figure 4:
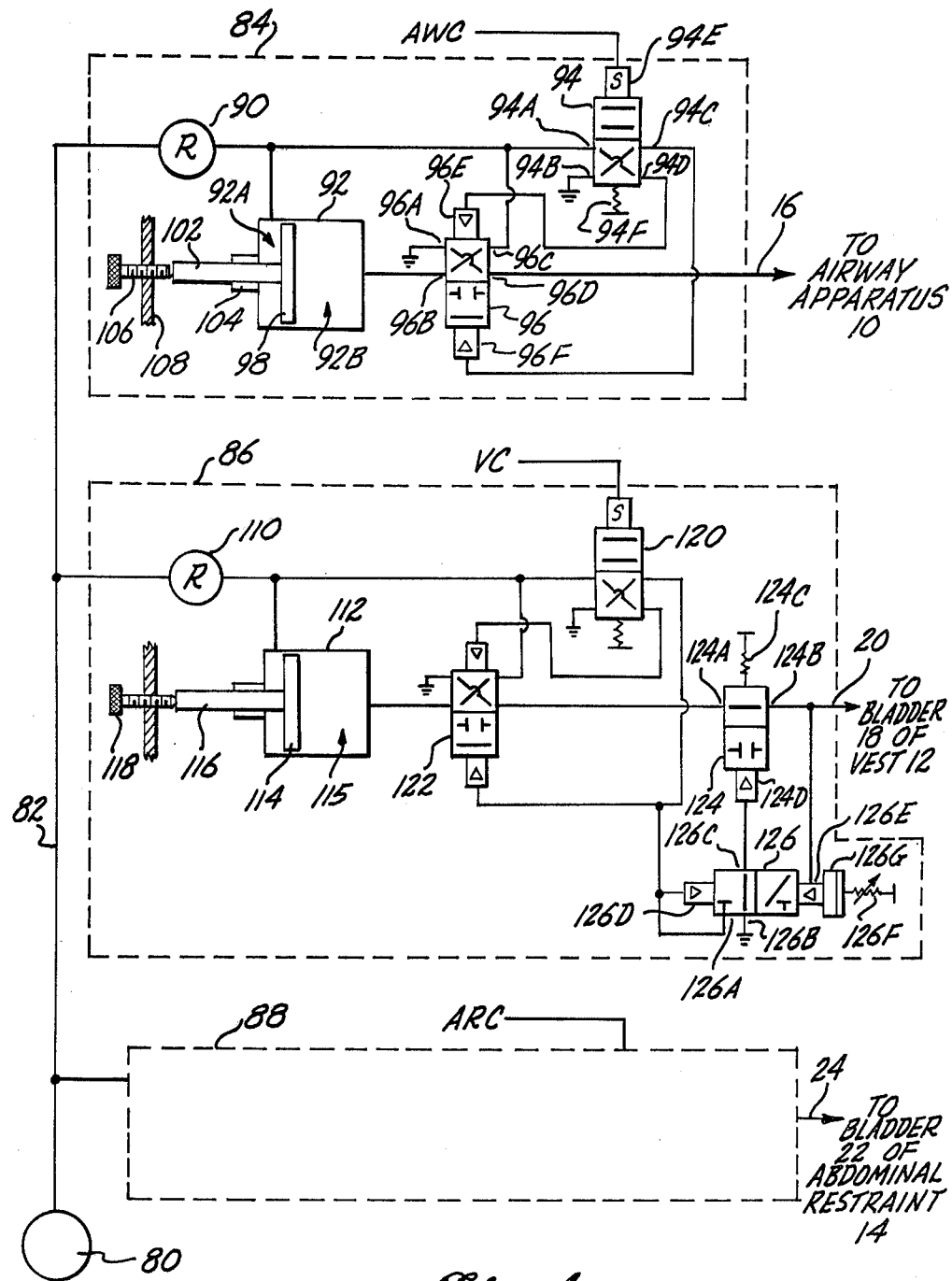
FIG. 4 is a fluid schematic diagram of a pneumatic portion of the apparatus that is coupled to the airway apparatus, to the vest, and to the abdominal restraint in FIG. 1.

With reference to FIG. 1, the apparatus includes an airway apparatus 10, a vest 12, and an abdominal restraint 14. Airway apparatus 10, which is coupled by a flexible conduit 16 to the pneumatic portion of the apparatus illustrated in FIG. 4, may comprise any conventional airway apparatus (such as a mask, an esophageal obturator airway, an esophageal pharyngeal airway, an endotracheal tube or a tracheotomy tube) that is designed to couple gas to and from the patient's lungs via the patient's airway. Vest 12 is adapted to be secured about the portion of the patient's body in the region of the thorax and includes an integral inflatable bladder 18 that overlies the patient's chest (and whose extent is indicated by dashed line 18A) and that is coupled to the pneumatic portion of the apparatus by a flexible conduit 20. Abdominal restraint 14 is adapted to be secured about the portion of the patient's body below the thorax and includes an integral inflatable bladder 22 that overlies the patient's abdomen (and whose extent is indicated by dashed line 22A) and that is coupled to the pneumatic portion of the apparatus by a flexible conduit 24.

As described in detail hereinafter, the pneumatic and electrical portions of the apparatus are constructed so as to permit the apparatus to operate in a ventilation mode, or in a CPR mode, or in a circulatory assistance mode.

In a typical operation of the apparatus when in the ventilation mode, bladders 18 and 22 are deflated. Gas containing or consisting of oxygen (that is obtained from a source of such a gas at a positive pressure above atmospheric pressure) and a source of gas at substantially atmospheric pressure (e.g., the atmosphere) are alternately coupled to airway apparatus 10 through conduit 16 so as to alternately inflate and deflate the patient's lungs through the airway. The rate of lung inflation and deflation (the ventilation rate) is selectively adjustable in a predetermined range (e.g., 5 to 20 Hz); the volume of gas that is introduced into the patient's lungs during inflation is selectively adjustable in a predetermined range (e.g., 0.1 to 2.0 liters); and, the duty-cycle of alternate lung inflation and deflation, i.e., the duration of an inflation relative to the duration of a successive deflation, is also selectively adjustable in a predetermined range (e.g., substantially 0% to substantially 100%).

In a typical operation of the apparatus when in the CPR mode, gas containing or consisting of oxygen and the atmosphere are alternately coupled in substantial synchronism to airway apparatus 10, to the bladder 18 of vest 12, and to the bladder 22 of abdominal restraint 14 via respective conduits 16, 20 and 24. As a result, the patient's lungs and bladders 18 and 22 are alternately inflated and deflated in substantial synchronism. The rate of alternate inflation and deflation (the CPR rate) is selectively adjustable in a predetermined range (e.g., 10 to 100 Hz); the volume of gas that is introduced into the patient's lungs during inflation is selectively adjustable in a predetermined range (e.g., 0.1 to 2.0 liters); the pressure that is obtained in the vest bladder during inflation is selectively adjustable in a predetermined range (e.g., 0 to 200 mm Hg); the pressure that is obtained in the abdominal restraint bladder during inflation is selectively adjustable in a predetermined range (e.g., 0 to 100 mm Hg); the duty-cycle of alternate lung inflation and deflation, the duty-cycle of alternate vest bladder inflation and deflation, and the duty-cycle of alternate abdominal restraint bladder inflation and deflation are selectively and individually adjustable in a predetermined range (e.g., substantially 0% to substantially 100%); and, the times at which the patient's lungs, the vest bladder, and the abdominal restraint bladder are inflated (and deflated) relative to each other are also selectively adjustable.

During an inflation-deflation cycle at the CPR rate, the concurrent inflation of the patient's lungs and the concurrent inflations of the vest and abdominal restraint bladders results in an increase in intrathoracic pressure so that blood is forced through the circulatory system. In addition, the gas that is forced into the lungs results in oxygenation of the blood as the blood passes through the lungs. The amount of CPR that is thus obtained, or, the efficiency of the apparatus in reproducing the pulmonary and cardiac functions of the patient, can be specifically tailored to the patient's needs by adjusting not only the CPR rate, but also the volume of gas that is introduced into the patient's lungs, the respective pressures obtained in the vest and abdominal restraint bladders, the duty-cycles of lung, vest bladder, and abdominal restraint bladder inflation and deflation, and the respective times at which the lungs, the vest bladder, and abdominal restraint are inflated and deflated relative to each other.

In a typical operation of the apparatus when in the circulatory assistance mode, the patient's lungs are inflated and deflated at the ventilation rate and in the manner previously described for the ventilation mode. Inflation and deflation of the vest and abdominal restraint bladders, however, is substantially asynchronous with respect to the ventilation rate and occurs at a rate that is related to the heart rate of the patient. The patient's electrical heart activity is monitored by sensing the patient's ECG signal and by detecting each R-wave therein (which represents the major pumping action of the heart caused by contraction of the left ventricle). The apparatus then operates either in a synchronized submode or an anticipated submode. In the synchronized submode, the vest and abdominal restraint bladders are each inflated (and subsequently deflated) at times substantially synchronous with the R-waves. In the anticipated submode, an average interval between successive R-waves, referred to as the average R-R interval (R-R), is determined and used to initiate inflation of the vest and abdominal restraint bladders at a time subsequent to each detected R-wave but typically prior to the anticipated time of arrival of the successive R-wave. In the anticipated submode, the time at which the vest and abdominal restraint bladders are inflated prior to the successive R-wave is selectively adjustable in a predetermined range (e.g., substantially 0 to 200 milliseconds), and the time over which the average R-R interval is determined is also adjustable. In both submodes, the vest bladder and abdominal restraint bladder may be inflated and deflated at a rate which is substantially equal to the patient's heart rate or which is a selected multiple of that heart rate, and the pressures that are obtained in the vest and abdominal restraint bladders, the duty-cycles of inflation and deflation thereof, and the relative times of inflation and deflation are selectively and individually adjustable as in the CPR mode.

Vest 12 includes a sheet 30 whose width is greater than the circumference of that portion of the patient's body in the region of the thorax. A second sheet 32 is disposed beneath that portion of sheet 30 that will overlie the patient's chest when the vest is in place, and the periphery 32A of sheet 32 is bonded to the underside of sheet 30 by an appropriate technique such as heat sealing (see FIG. 3) so as to define bladder 18. Sheet 30 is composed of a flexible, air-impermeable, washable and nonextensible material. Sheet 32 may be composed of a material similar to that of sheet 30, although the property of nonextensibility is not required. Straps 34 and 36 are provided for securing vest 12 about the patient, with the straps 34 and 36 being sewn or otherwise secured to sheet 30 at appropriate points and being of a length greater than the width of sheet 30. Respective ends of straps 34 and 36 terminate in respective mating parts of adjustable, quick-release connectors 38, 40. Preferably, the respective ends of straps 34 and 36 terminate above the chest portion of vest 12 so that connectors 38 and 40 are disposed in proximity to the chest portion. One of the ends of each of straps 34 and 36 may be moved relative to the associated mating part of respective connectors 38 and 40 so as to adjust the length of straps 34 and 36 when the respective mating parts of connectors 38 and 40 are assembled, thereby providing a secure fit of vest 12 about the patient's body notwithstanding the bodily dimensions of the patient.

It may be necessary to apply a defibrillation pulse to the patient while vest 12 is in place. To this end, vest 12 is provided with apertures 42 and 44 located in the chest portion of vest 12 respectively at the right side of the patient's chest between straps 34 and 36 and at the left side of the patient's chest above strap 34. Apertures 42 and 44 are each configured so as to permit a conventional defibrillator paddle electrode (one of which is illustrated in dashed outline in FIG. 3) to be inserted therethrough into contact with the skin of the patient's chest. As seen in FIGS. 2 and 3, apertures 42 and 44 are formed by providing corresponding apertures in sheets 30 and 32, and by securing the respective edges of the corresponding apertures in sheets 30 and 32 to each other. Reference, for example, aperture edges 30A and 32B defining aperture 42 (in FIG. 2) and aperture edges of 30B and 32C defining aperture 44 (in FIG. 3). It will be noted that bladder 18 encompasses and is formed around both apertures 42 and 44.

A portion 12A of vest 12 extends above strap 34, with aperture 44 being located in portion 12A. As can be appreciated, portion 12A is substantially unrestrained by strap 34 so that portion 12A tends to rise away from the patient's chest when bladder 18 is inflated. To resist this upward movement of portion 12A, a semirigid plate 46 (preferably of a lightweight plastic material) is disposed underneath sheet 30 in the region of portion 12A and maintained in place by a sheet 48 (of a material similar to that of sheets 30 and 32) whose periphery is secured to the underside of sheet 30. As illustrated in FIG. 3, a portion of plate 46 underlies strap 34, and the remaining portion of plate 46 extends to the top of portion 12A. Accordingly, when strap 34 is tightened, plate 46 resists upward movement of portion 12A upon inflation of bladder 18. As also illustrated in FIG. 3, plate 46 is provided with an aperture whose edges correspond to aperture edges 30B and 32C, whereby defibrillation aperture 44 is not blocked by plate 46.

Conduit 20 is coupled to bladder 18 by an elbow connector 48 that is centrally located in the chest portion of vest 12 between straps 34 and 36. Elbow connector 48 (preferably of a lightweight plastic material) may be secured to vest 12 in a manner similar to that in which plate 46 is so secured, e.g., by providing elbow connector 48 with a peripheral flange which abuts the underside of sheet 30 and by maintaining the peripheral flange in place by an underlying sheet of material that is secured to the underside of sheet 30. In order to limit the maximum pressure that may be developed in bladder 18 in the event of a malfunction in the pneumatic portion of the apparatus to be described, a pressure relief valve 50 (preferably composed of a lightweight plastic material) is located in the chest portion of vest 12 between straps 34 and 36 so as to communicate with bladder 18, and is secured to vest 12 in a manner similar to that described for elbow connector 48. Pressure relief valve 50 is of a type that will vent bladder 18 to the atmosphere whenever the pressure in bladder 18 exceeds a predetermined pressure value (e.g., 300 mm Hg) that is greater than the maximum pressure developed by the pneumatic portion of the apparatus during normal operation.

Abdominal restraint 14 is constructed in a manner similar to that described for vest 12. As such, abdominal restraint 14 includes a sheet 52 composed of a flexible, air-impermeable, nonextensible and washable material whose width is greater than the circumference of that portion of the patient's body immediately below the thorax, and a second sheet 53 of a similar material that is disposed below sheet 52 above the abdomen and whose peripheral edge is secured to the underside of sheet 52 by an appropriate technique so as to define bladder 22. Straps 54, 56 are sewn or otherwise secured to sheet 52 at appropriate points and have a greater length than the width of sheet 52, with respective ends of straps 54 and 56 terminating in respective mating parts of respective adjustable, quick-release connectors 58 and 60. Conduit 24 is coupled to bladder 18 by an elbow connector 62 centrally located in the abdominal portion of abdominal restraint 14 between straps 54 and 56, and a pressure relief valve 64 is also located in the abdominal portion of abdominal restraint 14 so as to vent bladder 22 to the atmosphere whenever the pressure therein exceeds a predetermined pressure value (e.g., 300 mm Hg) that is greater than the maximum pressure developed by the pneumatic portion of the apparatus during normal operation.

Although the sizes of vest 12, abdominal restraint 14 and of bladders 18 and 22 may be varied to fit a specific application, it has been found that more efficient CPR (and circulatory assistance) is obtained if the size of abdominal restraint 14 is similar to the size of vest 12, given the different physiologies of the respective body portions of the patient. In a working model of the apparatus, each of bladders 18 and 22 had a height of approximately 10 inches, a width of approximately 17 inches, and a volume of approximately 4 liters.

Turning now to the pneumatic portion of the apparatus illustrated in FIG. 4, a source 80 of pressurized gas containing or consisting of oxygen at a pressure within a predetermined range (e.g., 50–120 psi) is coupled by a conduit and manifold 82 to respective inlets of an airway pneumatic control apparatus 84, a vest pneumatic control apparatus 86, and an abdominal restraint pneumatic control apparatus 88.

Within airway pneumatic control apparatus 84, conduit and manifold 82 is coupled to the inlet of a conventional pressure regulator 90 which functions to provide a regulated pressure at its outlet (e.g., 45 psi) from the variable pressure applied to its inlet. The outlet of regulator 90 is coupled to a first side 92A of a pneumatic cylinder 92, to a port 94A of a pilot valve 94 (which comprises a four-way solenoid operated valve with spring return), and to a port 96C of a pilot-actuated valve (which comprises a four-way pressure operated valve). Ports 94B and 96A of valves 94 and 96 are coupled to the atmosphere, port 94C of valve 94 is coupled to a pressure control port 96F of valve 96, and port 94D of valve 94 is coupled to a pressure control port 96E of valve 96. Port 96B of valve 96 is coupled to a second side 92B of cylinder 92, and port 96D of valve 96 is coupled to conduit 16 going to airway apparatus 10.

Normally, valve 94 is maintained by return spring 94F in the marked position in FIG. 4, whereby port 94A is coupled with port 94D and port 94B is coupled with port 94C. However, whenever a signal AWC applied to a solenoid 94E of valve 94 has a predetermined logic level (e.g., a high logic level), valve 94 is moved to an alternate position wherein port 94A is coupled with port 94C and port 94B is coupled with port 94D. Valve 96 is moved to the marked position in FIG. 4 whenever positive pressure is applied to pressure control port 96E and positive pressure is removed from pressure control port 96F, whereby port 96A is coupled with port 96D and port 96B is coupled with port 96C. However, when positive pressure is removed from pressure control port 96E and applied to pressure control port 96F, valve 96 is moved to an alternate position, whereby ports 96A and 96C are each blocked and port 96B is coupled with port 96D.

Pneumatic cylinder 92 includes a piston 98 that defines respective sides 92A, 92B of cylinder 92. Piston 98 is supported on a shaft 102 which in turn passes through side 92A and which is supported by a bearing and seal structure 104, so that piston 98 is reciprocally movable within cylinder 92. The end of shaft 102 that extends from cylinder 92 is adapted to engage the end of a turn screw 106 rotatably secured in a wall 108 mounted in a fixed position relative to cylinder 92.

In operation, let it be assumed that signal AWC has a low logic level and that valve 94 is accordingly in the marked position in FIG. 4. When valve 94 is in the marked position, the pressure at the outlet of regulator 90 is coupled to pressure control port 96E of valve 96 through ports 94A and 94D, and pressure control port 96F is coupled to the atmosphere through ports 94C and 94B. Accordingly, valve 96 is maintained in the marked position illustrated in FIG. 4, whereby conduit 16 (and airway apparatus 10) is connected to the atmosphere through ports 96D and 96A. While valve 96 is in the marked position, it will be noted that the pressure at the outlet of pressure regulator 90 is coupled to side 92A of cylinder 92, and to side 92B of cylinder 92 through ports 96C and 96B of valve 96. Although the same pressure is thus applied to both sides of cylinder 92, the force exerted on that side of piston 98 facing side 92B is greater than the force exerted on that side of piston 98 facing side 92A (due to the reduction in piston surface area provided by shaft 102). Accordingly, piston 98 moves to the left so as to increase the volume of side 92A until the end of shaft 102 abuts the end of turn screw 106. It will be seen that as turn screw 106 is rotated so as to bring its end to or from cylinder 92, the maximum volume of side 92B that is obtained during the foregoing operation may be decreased and increased.

Let it now be assumed that signal AWC goes to a high logic level, whereby solenoid 94E is actuated. As a result, valve 94 moves to its alternate position, whereby the pressure at the outlet of regulator 90 is coupled to pressure control port 96F of valve 96 through ports 94A and 94C of valve 94 and pressure control port 96E is coupled to the atmosphere through ports 94D and 94B of valve 94. As a result, valve 96 moves to its alternate position, whereby side 92B of cylinder 92 is coupled to conduit 16 (and to airway apparatus 10) through ports 96B and 96D. At this time, it will be noted that the pressure at the outlet of regulator 90 is still being applied to side 92A of cylinder 92, but that the pressure at side 92B is at a lower value which is dependent to a certain extent on the pressure within the patient's lungs and therefore present at conduit 16. Accordingly, piston 98 moves to the right to decrease the volume of side 92B and to therefore discharge the gas therein into the patient's lungs. Preferably, cylinder 92 is designed so as to discharge the gas within side 92B in a manner so as to produce a rapid increase in pressure within the patient's lungs to a substantially constant value. When piston 98 has moved all the way to the right, it will be seen that the patient's lungs will have been inflated with the predetermined volume of gas selected by turn screw 106.

When signal AWC returns to a low logic level, valve 94 returns to the marked position in FIG. 4, causing valve 96 to return to the marked position in FIG. 4. As a result, the patient's lungs are deflated by coupling the gas therein to the atmosphere through airway apparatus 10, conduit 16, and ports 96D, 96A. At the same time that the patient's lungs are being deflated, side 92B of cylinder 92 is refilled with gas in the manner previously described and the cycle of lung inflation and deflation is repeated in response to the next set of successive changes in the logic level of signal AWC.

To summarize the operation of the airway pneumatic control apparatus 84, the volume of gas that is used to inflate the patient's lungs is selectively adjustable by turn screw 106 and the duty-cycle and relative time occurrences of lung inflation and deflation are established by the successive logic level changes in signal AWC.

The vest pneumatic control apparatus 86 includes similar components to those previously described for airway pneumatic control apparatus 84. That is, apparatus 86 includes a pressure regulator 110, a pneumatic cylinder 112 including a piston 114 and a shaft 116, a turn screw 118, a pilot valve 120, and a pilot-actuated valve 122. When a signal VC applied to the solenoid of valve 120 has a low logic level, valve 120 is in the marked position in FIG. 4, whereby valve 112 is maintained in the marked position in FIG. 4 so as to couple bladder 18 of vest 12 to the atmosphere and to couple the pressure at the outlet of regulator 110 to a side 115 of cylinder 112. As a result, bladder 18 is deflated and piston 114 is moved to the left until the end of shaft 116 engages the end of turn screw 118. At this time, a predetermined volume of gas is contained within side 115. When the signal VC goes to a high logic level, valve 120 moves to its alternate position, whereby valve 122 is caused to move to its alternate position so as to couple side 115 of cylinder 112 to bladder 18. Cylinder 112 is designed so as to discharge the gas within side 115 in a manner which produces a sharp increase in the pressure in bladder 18 to a pressure value established by the volume of air contained within side 115 and therefore selected by turn screw 118. When the signal VC returns to a low logic level, bladder 18 is deflated and side 115 of cylinder 112 is refilled with gas in the manner previously described.

In certain circumstances during the CPR and circulatory assistance modes, the pressure within bladder 18 may increase beyond the value selected by turn screw 118 due to the fact that pressure is also being exerted on the patient's body by the bladder 22 of abdominal restraint 14 and by lung inflation through airway apparatus 10. To limit the pressure in bladder 18 to the desired value (which is less than the maximum value established by pressure relief valve 50 in FIG. 1), valves 124 and 126 are provided in vest pressure control apparatus 86. Valve 124 (which comprises a two-way pressure operated valve with spring return) has a port 124A coupled to the port of valve 122 that is either coupled to the atmosphere or to side 115 of cylinder 112, and a port 124B that is coupled to conduit 20 going to bladder 18.

A spring 124C maintains valve 124 in the marked position in FIG. 4, whereby port 124A is coupled with port 124B. When positive pressure is applied to a pressure control port 124D of valve 124, valve 124 moves to an alternate position whereby ports 124A and 124B are each blocked. Valve 126 (which comprises a three-way adjustable amplifier relay valve) has a port 126A coupled to the port of valve 120 that is either coupled to the atmosphere or to the outlet of regulator 110, a port 126B coupled to the atmosphere, and a port 126C coupled to pressure control port 124D of valve 124. A pressure control port 126D of valve 126 is also coupled to the port of valve 120 that is either coupled to the atmosphere or to the outlet of regulator 110, and a pressure control port 126E of valve 126 is coupled to conduit 20.

If it is now assumed that signal VC has a high logic level and that valve 120 is in its alternate position, it will be noted that the pressure applied by valve 120 to pressure control port 126D of valve 126 moves valve 126 to the marked position in FIG. 4, whereby port 126A is blocked and port 126B is coupled with port 126C. As a result, port 124D of valve 124 is supplied with atmospheric pressure, whereby spring 124C maintains valve 124 in the marked position in FIG. 4 so as to couple valve 122 (and side 115 of cylinder 112) to conduit 20 (and thus bladder 18) through ports 124A and 124B. Valve 126 also has an adjustable spring 126F and an associated diaphragm 126G, each operatively associated with pressure control port 126E. When the pressure in bladder 18 (and thus in conduit 20) exceeds a desired value selected by the setting of adjustable spring 126F, valve 126 moves to an alternate position wherein port 126B is blocked and port 126A is coupled with port 126C. As a result, the pressure at port 126A is coupled through port 126C to pressure control port 124D of valve 124, thereby moving valve 124 to its alternate position, whereby ports 124A and 124B thereof are each blocked. Accordingly, the pressure within bladder 18 is maintained at the desired value and further inflation of bladder 18 is inhibited.

When signal VC subsequently goes to a low logic level, valve 120 causes atmospheric pressure to be applied to port 126A of valve 126 and thus to pressure control port 124D of valve 124 through port 126C. As a result, valve 124 returns to the marked position in FIG. 4, whereby bladder 18 is vented to the atmosphere through valve 124 and valve 122. The pressure in conduit 20 and therefore at pressure control port 126E of valve 126 accordingly also drops. When signal VC subsequently returns to a high logic level, valve 120 again causes pressure to be applied to pressure control port 126D of valve 126, whereby valve 126 moves to the marked position in FIG. 4 and the previously described pressure regulation operation may be repeated.

To summarize, the pressure that is provided in bladder 18 during inflation thereof is established by the setting of turn screw 118 and by the setting of adjustable spring 126F of valve 126, and the duty-cycle and relative time occurrences of vest bladder inflation and deflation are established by the successive logic level changes in signal VC.

The abdominal restraint pneumatic control apparatus 88 is constructed and operates in a manner identical to that described for vest pneumatic control apparatus 86. As such, the pressure that is provided in bladder 22 during inflation thereof is established by the setting of an adjustable turn screw and by the setting of an adjustable spring of an adjustable amplifier relay valve, and the duty-cycle and relative time occurrences of abdominal restraint bladder inflation and deflation are determined by the successive logic level changes in a signal ARC applied to a pilot valve of apparatus 88.

Figure 5:
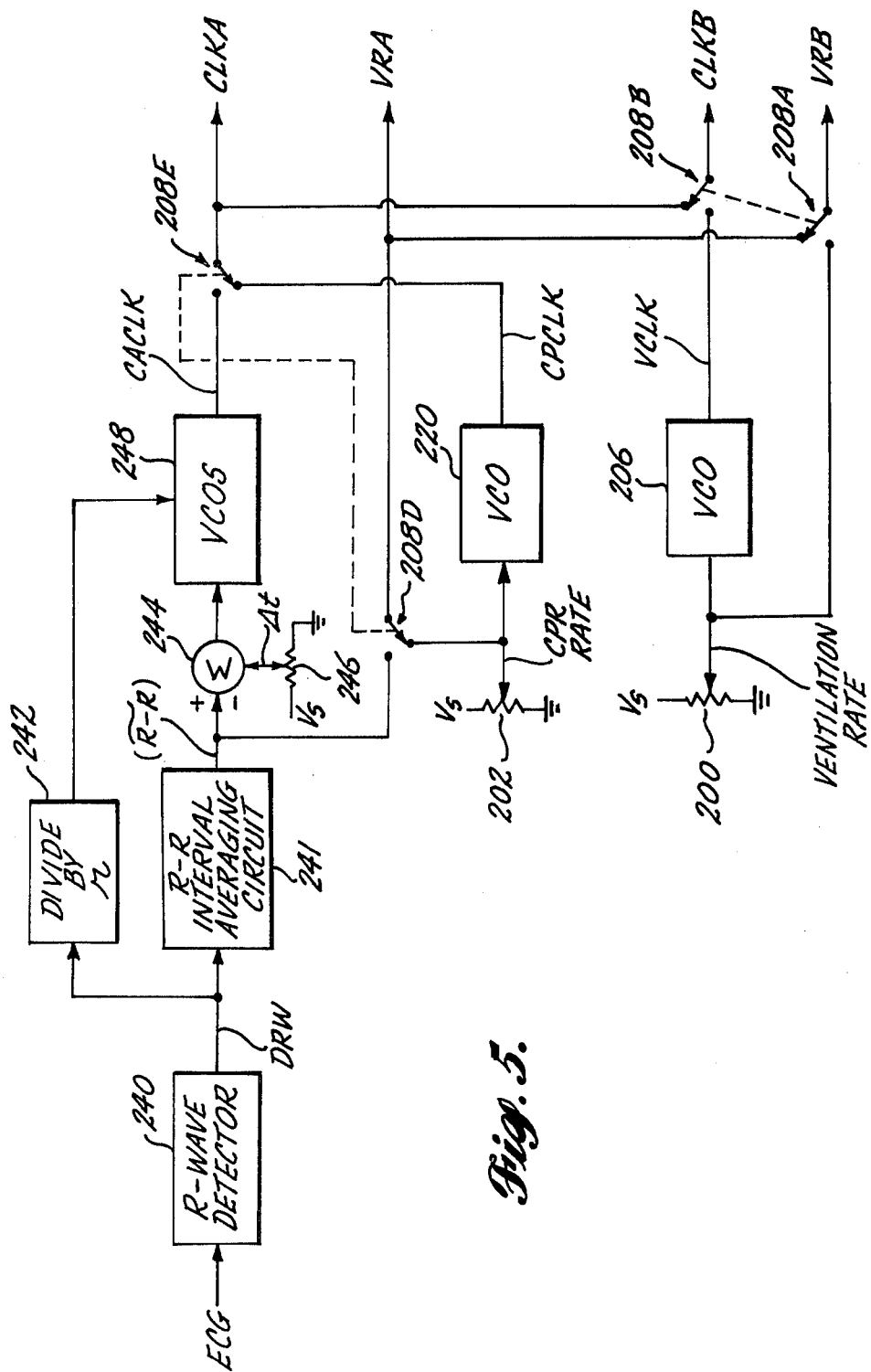
FIGS. 5 and 6 are electrical block diagrams of an electrical portion of the apparatus which is particularly adapted to control the pneumatic portion of the apparatus in FIG. 4.
Figure 6:
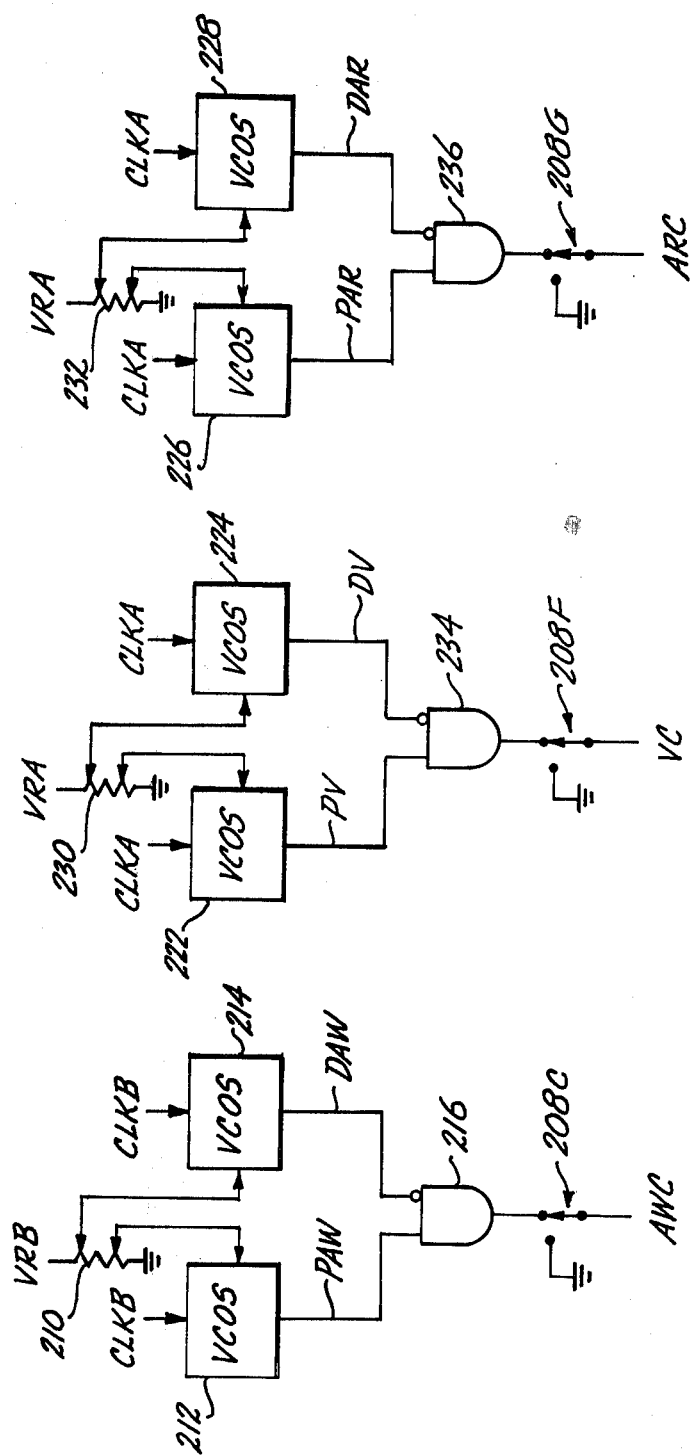

Turning now to the electrical portion of the apparatus illustrated in FIGS. 5 and 6, it will be remembered that the rate of lung inflation and deflation is controlled at an adjustable ventilation rate during both the ventilation and circulatory assistance modes, that the rates of lung, vest bladder, and abdominal restraint bladder inflation and deflation are controlled at an adjustable CPR rate during the CPR mode, and that the rates of vest bladder and abdominal restraint bladder inflation and deflation are controlled at a rate related to the electrical heart activity of the patient during the circulatory assistance mode.

In FIG. 5, the ventilation rate is adjusted by the setting of the tap of a potentiometer 200 coupled between a source of supply potential $V_S$ and ground potential so as to produce a VENTILATION RATE signal comprising a voltage that decreases in magnitude as the selected ventilation rate increases, and vice-versa. The CPR rate is adjusted by the setting of the tap of a potentiometer 202 connected between the source of supply potential $V_S$ and ground potential so as to produce a CPR RATE signal comprising a voltage that decreases in magnitude as the selected CPR rate increases, and vice-versa. The rate of vest and abdominal restraint bladder inflation and deflation during the circulatory assistance mode is determined by an output signal DRW from an R-wave detector 240 responsive to an ECG signal obtained from the patient.

The VENTILATION RATE signal is applied to the input of a voltage-controlled oscillator 206 which provides an output signal VCLK whose frequency is inversely proportional to the magnitude of the voltage at the input of oscillator 206 rate and therefore proportional to the selected ventilation rate. The VENTILATION RATE signal and the signal VCLK are applied to respective contact sets 208A, 208B of a mode control switch which can be used to select either the ventilation mode, the CPR mode, or the circulatory assistance mode. When the ventilation mode has been selected, contact sets 208A, 208B are in positions alternate to those marked in FIG. 5 whereby the VENTILATION RATE signal is coupled to the portion of the apparatus in FIG. 6 as signal VRB and signal VCLK is coupled to the portion of the apparatus in FIG. 6 as signal CLKB.

Referring now to FIG. 6, signal VRB is applied to one side of a potentiometer 210 whose other side is coupled to ground potential. Potentiometer 210 is provided with two taps, the lower of which is coupled to the signal input of a voltage-controlled one-shot 212 and the upper of which is coupled to the signal input of a voltage-controlled one-shot 214. The two taps of potentiometer 210 are constructed and arranged so that the voltage appearing on the lower tap going to one-shot 212 has a lesser magnitude than the voltage on the upper tap going to one-shot 214. The trigger inputs of one-shots 212 and 214 are each supplied with signal CLKB, and one-shots 212 and 214 are each constructed so as to provide an output signal that goes to a predetermined logic level (e.g., a low logic level) upon the occurrence of a predetermined logic level transition in signal CLKB (e.g., a low-high logic level transition) and that goes to another logic level (e.g., a high logic level) at a subsequent time determined by the magnitude of the voltage applied to the signal input thereof. The output signal from one-shot 212, denominated PAW, is coupled to a noninverting input of an AND gate 216, and the output signal from one-shot 214, denominated DAW, is coupled to an inverting input of AND gate 216. The output signal from AND gate 216 is coupled to a contact set 208C of the mode control switch. When contact set 208C is in the marked position in FIG. 6, the output signal from AND gate 216 comprises signal AWC that is supplied to the airway pneumatic control apparatus 84 (FIG. 4) as previously described. When contact set 208C is in the alternate position in FIG. 5, signal AWC is maintained at a low logic level (e.g., ground potential).

Figure 7:
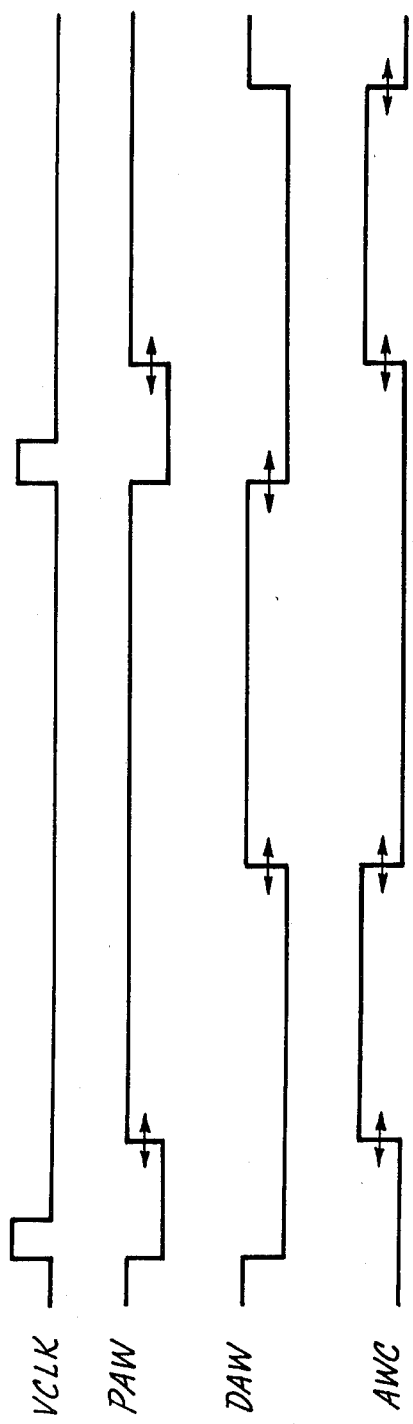
FIG. 7 is a timing diagram illustrating the operation of the electrical portion of the apparatus in FIGS. 5 and 6 during ventilation.

When the ventilation mode has been selected, contact sets 208A and 208B are in the alternate positions in FIG. 5 and contact set 208C is in the marked position in FIG. 6. It will be apparent from the discussion hereinafter that when the ventilation mode has been selected, signals VC and ARC are maintained at a low logic level so that the vest bladder and the abdominal restraint bladder remain deflated. With additional reference now to FIG. 7, signal VCLK comprises a train of pulses that occur at the selected ventilation rate. At the leading edge of each pulse in signal VCLK, one-shots 212 and 214 initiate low logic levels in their respective output signals PAW and DAW whereupon signal AWC from AND gate 216 is also at a low logic level. At a subsequent time determined by the setting of the corresponding tap on potentiometer 210, one-shot 212 terminates the low logic level in output signal PAW whereupon signal AWC from AND gate 216 goes to a high logic level to initiate inflation of the lungs as previously described. At a subsequent time determined by the setting of the corresponding tap on potentiometer 210, one-shot 214 terminates the low logic level in output signal DAW whereupon signal AWC from AND gate 216 returns to a low logic level to terminate inflation of the lungs and to initiate deflation of the lungs. As can be seen, the cycle just described is repeated upon the occurrence of the next pulse in signal VCLK.

It will be recognized that the desired ventilation rate is established by signal VCLK (and selected by the setting of the tap of potentiometer 200); and the duty-cycle and relative time occurrences of lung inflation and deflation are established by the successive low-high logic level transitions in signals PAW and DAW (and selected by the setting of the corresponding taps on potentiometer 210). As the selected ventilation rate is increased or decreased, the voltage of the VENTILATION RATE signal (and therefore the voltage of signal VRB) is proportionally decreased or increased so as to proportionately decrease or increase the duration of the low logic levels in signals PAW and DAW, whereby the duty-cycle of lung inflation and deflation is maintained substantially constant notwithstanding changes in the selected ventilation rate.

Returning now to FIG. 5, the CPR RATE signal is applied to the input of a voltage-controlled oscillator 220 which provides an output signal CPCLK whose frequency is inversely proportional to the magnitude of the signal at the input of oscillator 220 and therefore proportional to the selected CPR rate. The CPR RATE signal and the signal CPCLK are coupled to respective contact sets 208D and 208E of the mode control switch. When the CPR mode has been selected, contact sets 208D and 208E are in the marked positions in FIG. 5 whereupon the signal CPCLK and the CPR RATE signal are coupled to the portion of the apparatus in FIG. 6 as signals CLKA and VRA. It will also be noted that when the CPR mode has been selected, contact sets 208A and 208B are also in the marked positions in FIG. 5 whereupon the signal CPCLK and the CPR RATE signal are coupled to the portion of the apparatus in FIG. 6 as signals CLKB and VRB.

As illustrated in FIG. 6, signal CLKA is applied to the trigger inputs of respective voltage-controlled one-shots 222, 224, 226 and 228. Signal VRA is coupled to one side of each of potentiometers 230 and 232 whose other sides are coupled to ground potential. A lower tap of potentiometer 230 is coupled to the signal input of one-shot 222; an upper tap of potentiometer 230 is coupled to the signal input of one-shot 224; a lower tap of potentiometer 232 is coupled to the signal input of one-shot 226; and, an upper tap of potentiometer 232 is coupled to the signal input of one-shot 228. The output signal from one-shot 222, denominated PV, is coupled to a noninverting input of an AND gate 234; the output signal from one-shot 224, denominated DV, is coupled to an inverting input of AND gate 234; the output signal from one-shot 226, denominated PAR, is coupled to a noninverting input of an AND gate 236; and, the output signal from one-shot 228, denominated DAR, is coupled to an inverting input of AND gate 236. The output signal from AND gate 234 is coupled to a contact set 208F of the mode control switch, and the output signal from AND gate 236 is coupled to a contact set 208G of the mode control switch. When contact sets 208F and 208G are in the marked positions in FIG. 6, the output signals from AND gates 234 and 236 are respectively coupled to the vest pneumatic control apparatus 86 and the abdominal restraint pneumatic control apparatus 88 in FIG. 4 as signals VC and ARC. When contact sets 208F and 208G are in the alternate positions in FIG. 5, signals VC and ARC are maintained at a low logic level.

Figure 8:
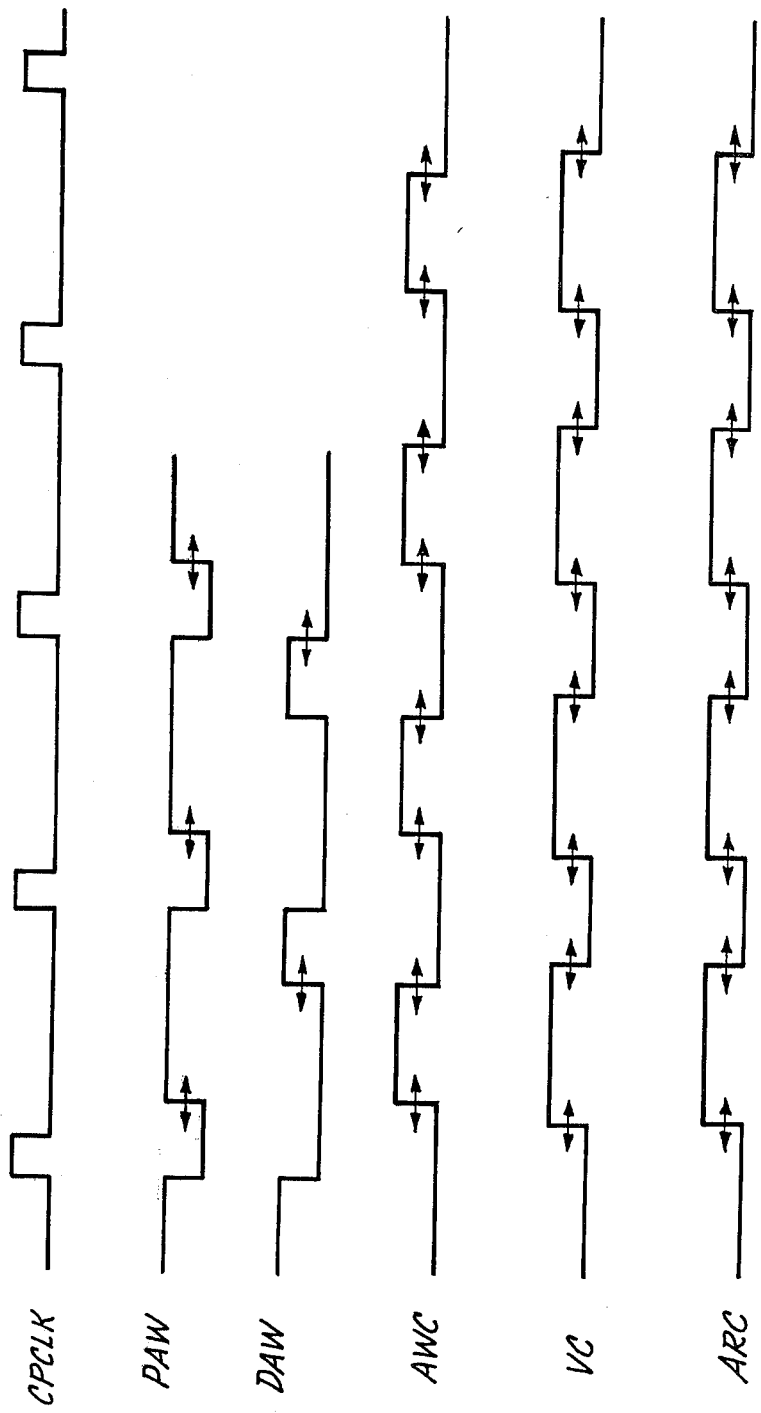
FIG. 8 is a timing diagram illustrating the operation of the electrical portion of the apparatus during CPR; and, FIG. 9 is a timing diagram illustrating the operation of the electrical portion of the apparatus during circulatory assistance.

When the ventilation mode has been selected, contact sets 208F and 208G are in the marked positions in FIG. 6 so that signals VC and ARC remain at a low logic level, whereupon the bladder 18 of vest 12 and the bladder 22 of abdominal restraint 14 remain deflated. When the CPR mode has been selected, all of the contact sets 208A–208G are in the marked positions in FIGS. 5 and 6. Referring also now to FIG. 8, signal CPCLK comprises a train of pulses occurring at the selected CPR rate. The operation of one-shots 212 and 214 is similar to that previously described for the ventilation mode. One-shots 212 and 214 each initiate a low logic level in their respective output signals PAW and DAW at the leading edge of each pulse in signal CPCLK (which is applied to one-shots 212 and 214 as signal CLKB), and terminate their respective low logic levels at successive times determined by the setting of the corresponding taps on potentiometer 210 and also determined by the magnitude of the voltage of the CPR RATE signal (which is applied to potentiometer 210 as signal VRB). The successive low-high logic level transitions in signals PAW and DAW determine the time during which signal AWC has a high logic level and thus determine the duty-cycle and relative time occurrences of lung inflation and deflation.

One-shots 222 and 224 and one-shots 236 and 228 operate in a similar manner to that previously described for one-shots 212 and 214. That is, low logic levels are initiated in output signals PV, DV, PAR and DAR at the initiation of each pulse in signal CPCLK (which is applied to one-shots 222, 224, 226 and 228 as signal CLKA) and are terminated at respective times determined by the setting of the corresponding taps on potentiometers 230 and 232 and by the magnitude of the voltage of the CPR RATE signal (which is applied to potentiometers 230 and 232 as signal VRA). The successive low-high logic level transitions in signals PV and DV determine the time during which signal VC has a high logic level and thus determine the duty-cycle and relative time occurrences of vest bladder inflation and deflation. The successive low-high logic level transitions in signals PAR and DAR determine the time during which signal ARC has a high logic level and thus determine the duty-cycle and relative time occurrences of abdominal restraint bladder inflation and deflation. As can be appreciated from the foregoing description, the lungs, the vest bladder, and the abdominal restraint bladder are inflated (and deflated) in substantial synchronism at the selected CPR rate and at selected times relative to each other.

Figure 9:
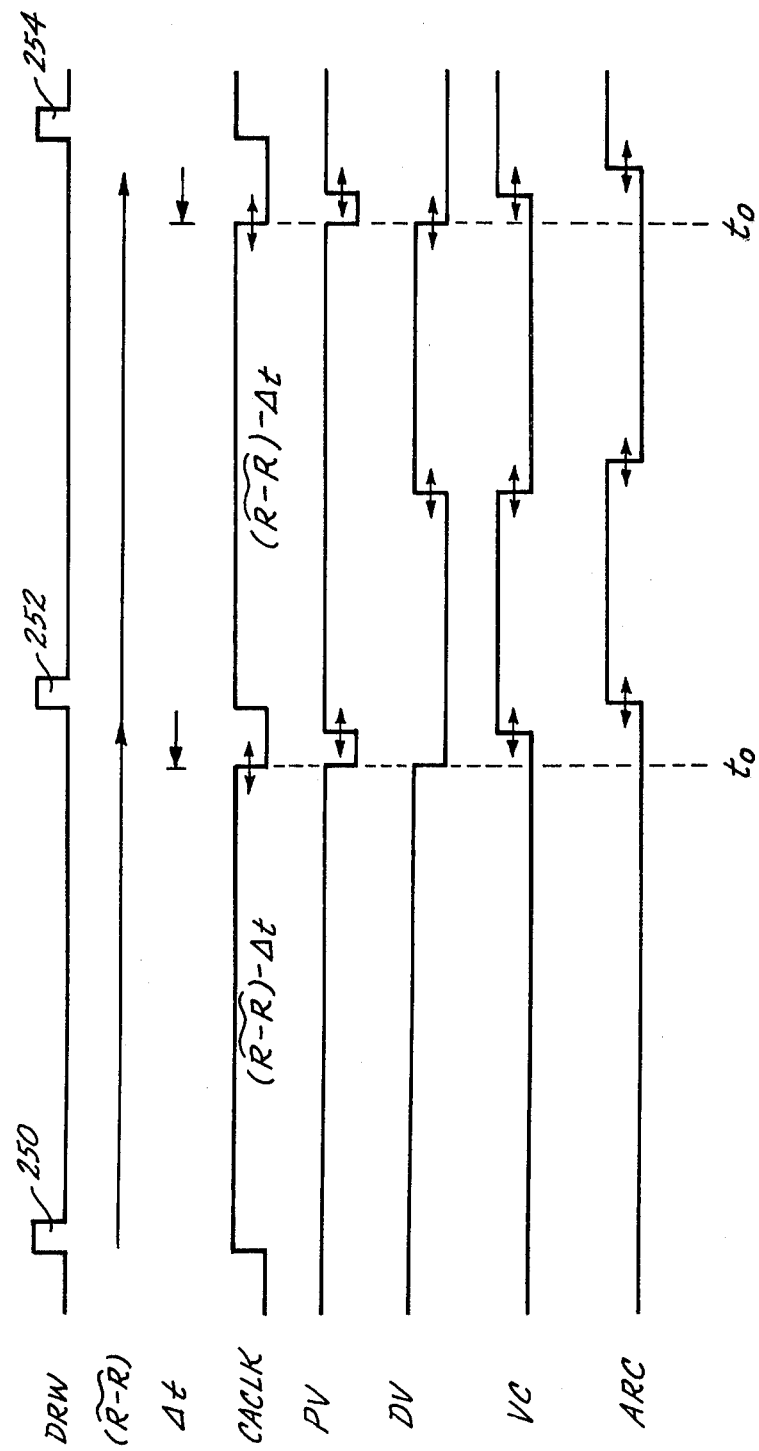

Returning to FIG. 5, an ECG signal is obtained from a conventional heart monitor (which may be responsive to conventional electrodes mounted on the patient's body) and supplied to the input of R-wave detector 240. As previously noted, each R-wave in the ECG signal is synchronous with the major pumping action of the heart caused by ventricular contraction. R-wave detector 240 provides an output signal DRW which, as seen in FIG. 9, comprises a train of pulses, each of which is initiated substantially at the initiation of an R-wave in the ECG signal and which is terminated substantially upon the termination of an R-wave in the ECG signal. Output signal DRW is applied to the input of an R—R interval averaging circuit 241 and to the input of a divide-by-n circuit 242. The output signal $(\widetilde{R-R})$ from circuit 241 comprises a voltage whose magnitude is proportional to the average R—R interval as determined by circuit 204 from the successive pulses in signal DRW in accordance with a predetermined relationship such as:

$$(\widetilde{R\text{-}R}) = \frac{m \times \text{PREVIOUS } (\widetilde{R\text{-}R}) + \text{NEW } (R\text{-}R)}{m + 1}$$

where:
  m is an integer (e.g., 2, 3 ...) representing the number of previous R—R intervals over which the average is taken;
  PREVIOUS $(\widetilde{R-R})$ is a previously determined average R—R interval over m such intervals; and
  NEW (R—R) is the most recently determined R—R interval.

Output signal $(\widetilde{R-R})$ is applied to a positive input of a summing junction 244 and coupled to contact set 208F of the mode control switch. A signal Δt is applied to a negative input of summing junction 244, with signal Δt comprising a voltage that is obtained from the tap of a potentiometer 246 coupled between the source of supply potential $V_S$ and ground potential. As will be apparent from the ensuing discussion, the voltage of signal Δt is zero when the apparatus is to be operated in the synchronized submode, and the voltage of signal Δt has a positive value when the apparatus is to be operated in the anticipated submode. The output signal from summing junction 244, or $(\widetilde{R-R})$-Δt, is applied to the signal input of a voltage-controlled one-shot 248 to whose trigger input is applied to the output signal from divide-by-n circuit 242. The output signal from one-shot 248, denominated CACLK, is coupled to contact set 208D of the mode control switch.

When in the circulatory assistance mode, contact sets 208A, 208B, 208D and 208E of the mode control switch are in the alternate positions in FIG. 5, and contact sets 208C, 208F and 208G of the mode control switch are in the marked positions in FIG. 6. Accordingly, signal VCLK and the VENTILATION RATE signal are supplied to the portion of the apparatus in FIG. 6 as signals CLKB and VRB so that the patient's lungs are inflated and deflated at times controlled by the successive logic level changes in signal AWC and at the selected ventilation rate. Signal CACLK and the signal (R—R) are applied to the portion of the apparatus in FIG. 7 as signals CLKA and VRA, whereby the vest bladder and the abdominal restraint bladder are inflated and deflated in relation to the average R—R interval and in the manner to be described with reference to FIG. 9.

Let it be assumed that the divisor n in divide-by-n circuit 242 is one, and that the output signal from circuit 242 accordingly comprises a train of pulses identical to those illustrated for signal DRW. At the leading edge of each pulse in signal DRW, the output signal CACLK from one-shot 248 (and signal CLKA) undergoes a low-high logic level transition. As will be appreciated from the following discussion, a previous detected R-wave (e.g., that represented by pulse 250 in signal DRW) is used to trigger a determination of the time of vest bladder and abdominal restraint bladder inflation with respect to a subsequent R-wave (e.g., that represented by pulse 252 in signal DRW). The amount of time that signal CACLK (and signal CLKA) remains at a high logic level following each such low-high logic level transition is dependent on the magnitude of the voltage applied to the signal input of one-shot 248, i.e., the magnitude of the voltage of signal (R—R)-$\Delta$t. If the apparatus is operating in the synchronized submode and $\Delta$t is zero, signal CACLK (and signal CLKA) returns to a low logic level at a time $t_0$ which may be substantially equal to the actual time at which the next R-wave is initiated (e.g., pulse 252), or before the actual time of the next R-wave (e.g., pulse 254). When signal CACLK (and signal CLKA) returns to a low logic level, one-shots 222 and 224 cause signals PV and DV to go to a low logic level (and one-shots 226 and 228 cause signals PAR and DAR to go to a low logic level). At respective times determined by the setting of the corresponding taps on potentiometers 230 and 232 and by the magnitude of the voltage of signal (R—R), one-shots 222 and 224 cause signals PV and DV to return to a high logic level, and one-shots 226 and 228 cause signals PAR and DAR to return to a high logic level. As previously discussed, signal VC has a high logic level from the time of a low-high logic level transition in signal PV to the time of a low-high logic level transition in signal DV, and signal ARC has a high logic level from the time of a low-high logic level transition in signal PAR to the time of a low-high logic level transition in signal DAR. Accordingly, when the apparatus is operating in the synchronized submode and $\Delta$t is zero, the vest bladder and abdominal restraint bladder are inflated (and deflated) in relation to the average R—R interval and substantially synchronized with the actual R—R interval.

In many situations, it is desirable to inflate both the vest bladder and the abdominal restraint bladder prior to the anticipated time of each R-wave, so that the intrathoracic pressure generated thereby substantially assists the heart in circulating blood through the body. In these situations, the anticipated submode is used and $\Delta$t is chosen (by adjusting the setting of the tap of potentiometer 206) to be a positive value representing the time prior to the anticipated time of the next R-wave that inflation of the vest bladder and of the abdominal restraint bladder is to be initiated. The anticipated submode is particularly illustrated in FIG. 9, wherein it can be seen that signal CACLK returns to a low logic level following each of pulses 250 and 252 at a time $t_0$ which is $\Delta$t before the anticipated time of arrival of the next R-wave (represented by (R—R)). It will be appreciated that the time occurrences of the successive low-high and high-low logic level transitions in signals VC and ARC will each be advanced in time by an amount equal to $\Delta$t, whereby inflation of both the vest bladder and the abdominal restraint bladder may be chosen to begin at respective times which are before the anticipated time of arrival of the next R-wave.

As with the CPR mode, the duty-cycles and time occurrences of vest bladder inflation (and deflation) and of abdominal restraint bladder inflation (and deflation) relative to each other can be varied by adjusting the setting of the corresponding taps of potentiometers 230 and 232.

In some situations, it may be desirable to provide vest bladder and abdominal restraint bladder inflation and deflation at an interval which is a multiple of the average R—R interval. Accordingly, the divisor n in divide-by-n circuit 242 is chosen to be a integer greater than one and equal to the desired multiple. As a result, the actual interval between successive pulses in the output signal from circuit 242 will be n times the interval between successive pulses in signal DRW. Accordingly, one-shot 248 is triggered every nth pulse in signal DRW, so that signals VC and ARC go to a high logic level at an interval determined by (R—R)-$\Delta$t following each such nth pulse.

While the invention has been described with reference to a preferred embodiment and with reference to certain operations within the ventilation, CPR, and circulatory assistance modes, it is to be clearly understood by those skilled in the art that the invention is not limited thereto. For example, the mode switch may be constructed so as to permit lung inflation, vest bladder inflation, or abdominal restraint inflation to be selectively inhibited in any mode (by moving respective contact sets 208C, 208F or 208G in FIG. 6 to the alternate positions). As another example, abdominal restraint pneumatic control apparatus 82 may be controlled so as to maintain the abdominal restraint bladder fully inflated or fully deflated during the CPR and circulatory assistance modes. Therefore, the scope of the invention is to be interpreted only in conjunction with the appended claims.

The embodiments of the invention in which an exclusive property or privilege is claimed are defined:

1. An apparatus for assisting and reproducing the pulmonary and cardiac functions of a patient, said apparatus comprising:
   an airway apparatus constructed so as to be placed during use in proximity to the patient's airway to provide fluid communication with the patient's lungs;
   a vest constructed so as to be secured during use about the portion of the patient's body in the region of the thorax, said vest including an inflatable bladder that overlies the patient's chest;

an abdominal restraint constructed so as to be secured during use about the portion of the patient's body immediately below the thorax, said abdominal restraint including an inflatable bladder that overlies the patient's abdomen; and, control means that is in fluid communication with said airway apparatus, said vest bladder, and said abdominal restraint bladder, said control means being operable to alternately inflate and deflate, in substantial synchronism, said vest bladder, said abdominal restraint bladder, and the patient's lungs through said airway apparatus.

2. An apparatus as recited in claim 1, wherein said control means is in fluid communication with a source of gas at a positive pressure above atmospheric pressure and a source of gas at substantially atmospheric pressure, said control means including:

airway pneumatic control means in fluid communication with said airway apparatus and responsive to respective first and second states in an airway control signal to respectively inflate the patient's lungs by coupling gas obtained from said source of gas at a positive pressure to said airway apparatus and deflate the patient's lungs by coupling said airway apparatus to said source of gas at substantially atmospheric pressure;

vest pneumatic control means in fluid communication with said vest bladder and responsive to respective first and second states in a vest control signal to respectively inflate said vest bladder by coupling gas obtained from said source of gas at a positive pressure to said vest bladder and deflate said vest bladder by coupling said vest bladder to said source of gas at substantially atmospheric pressure;

abdominal restraint pneumatic control means in fluid communication with said abdominal restraint bladder and responsive to first and second states in an abdominal restraint control signal to respectively inflate said abdominal restraint bladder by coupling gas obtained from said source of gas at a positive pressure to said abdominal restraint bladder and deflate said abdominal restraint bladder by coupling said abdominal restraint bladder to said source of gas at substantially atmospheric pressure; and, electronic control means supplying said airway control signal, said vest control signal, and said abdominal restraint control signal to said airway pneumatic control means, said vest pneumatic control means, and said abdominal restraint pneumatic control means, respectively, said electronic control means being adapted to selectively vary the timing of the respective first and second states in said airway, vest and abdominal restraint control signals while maintaining said first and second states in said signals in substantial synchronism with each other.

3. An apparatus as recited in claim 2, wherein said airway pneumatic control means is adapted to inflate the patient's lungs with a predetermined volume of gas.

4. An apparatus as recited in claim 3, wherein said airway pneumatic control means includes means for selectively adjusting said predetermined volume of gas.

5. An apparatus as recited in claim 2, wherein said vest pneumatic control means is adapted to inflate said vest bladder to a predetermined pressure value.

6. An apparatus as recited in claim 5, wherein said vest pneumatic control means includes means for selectively adjusting said predetermined pressure value.

7. An apparatus as recited in claim 2, wherein said abdominal restraint pneumatic control means is adapted to inflate said abdominal restraint bladder to a predetermined pressure value.

8. An apparatus as recited in claim 7, wherein said abdominal restraint pneumatic control means includes means for selectively adjusting said predetermined pressure value.

9. An apparatus as recited in claim 2, wherein said electronic control means includes means for selecting a CPR mode of operation; and, wherein said electronic control means is operative when said CPR mode has been selected to alternate said first and second states in each of said airway, vest and abdominal restraint control signals at a predetermined CPR rate, whereby the patient's lungs, said vest bladder, and said abdominal restraint bladder are each alternately inflated and deflated at said predetermined CPR rate.

10. An apparatus as recited in claim 1, wherein said electronic control means includes means for selectively adjusting said predetermined CPR rate.

11. An apparatus as recited in claim 9, wherein said electronic control means includes means for selectively adjusting the duty-cycle of said alternate first and second states in said airway control signal.

12. An apparatus as recited in claim 9, wherein said electronic control means includes means for selectively adjusting the duty-cycle of said alternate first and second states in said vest control signal.

13. An apparatus as recited in claim 9, wherein said electronic control means includes means for selectively adjusting the duty-cycle of said alternate first and second states in said abdominal restraint control signal.

14. An apparatus as recited in claim 1, wherein said control means includes means for selecting a ventilation mode of operation, a CPR mode of operation, and a circulatory assistance mode of operation; wherein said control means is operative when said ventilation mode has been selected to deflate said vest bladder and said abdominal restraint bladder and to alternately inflate and deflate the patient's lungs through said airway apparatus at a predetermined ventilation rate; wherein said control means is operative when said CPR mode has been selected to alternately inflate and deflate the patient's lungs through said airway apparatus, to alternately inflate and deflate said vest bladder, and to alternately inflate and deflate said abdominal restraint bladder, in substantial synchronism with each other at a predetermined CPR rate; and, wherein said control means is operative when said circulatory assistance mode has been selected to alternately inflate and deflate the patient's lungs through said airway apparatus at said ventilation rate, and to alternately inflate and deflate said vest bladder and said abdominal restraint bladder in substantial synchronism with each other at a circulatory assistance rate related to the measured heart rate of the patient.

15. An apparatus as recited in claim 14, wherein said control means is adapted to inflate the patient's lungs with a predetermined volumn of gas.

16. An apparatus as recited in claim 15, wherein said control means includes means for selectively adjusting said predetermined volumn of gas.

17. An apparatus as recited in claim 14, wherein said control means is operative to inflate said vest bladder to a predetermined pressure value.

18. An apparatus as recited in claim 17, wherein said control means includes means for selectively adjusting said predetermined pressure value.

19. An apparatus as recited in claim 14, wherein said control means is operative to inflate said abdominal restraint bladder to a predetermined pressure value.

20. An apparatus as recited in claim 19, wherein said control means includes means for selectively adjusting said predetermined pressure value.

21. An apparatus as recited in claim 14, wherein said control means includes means for selectively adjusting said predetermined ventilation rate.

22. An apparatus as recited in claim 14, wherein said control means includes means for selectively adjusting the duty-cycle of alternate lung inflation and deflation.

23. An apparatus as recited in claim 14, wherein said control means includes means for selectively adjusting said predetermined CPR rate.

24. An apparatus as recited in claim 14, wherein said control means includes means for selectively adjusting the duty-cycle of alternate vest bladder inflation and deflation.

25. An apparatus as recited in claim 14, wherein said control means includes means for selectively adjusting the duty-cycle of alternate abdominal restraint bladder inflation and deflation.

26. An apparatus as recited in claim 14, wherein said control means includes means for selectively adjusting the relative phasing of lung, vest bladder, and abdominal restraint bladder inflation and deflation when said CPR mode has been selected.

27. An apparatus as recited in claim 14, wherein said control means includes means for selectively adjusting the relative phasing of vest bladder and abdominal restraint bladder inflation and deflation when said circulatory assistance mode has been selected.

28. An apparatus as recited in claim 14, wherein said control means includes means for selectively inhibiting lung inflation, vest bladder inflation and abdominal restraint bladder inflation when any of said modes has been selected.

29. An apparatus as recited in claim 1, wherein said control means includes means for selecting a ventilation mode of operation, a CPR mode of operation and a circulatory assistance mode of operation; wherein said control means is operative when said ventilation mode has been selected to deflate said vest bladder and said abdominal restraint bladder and to alternately inflate and deflate the patient's lungs through said airway apparatus at a predetermined ventilation rate; wherein said control means is operative when said CPR mode has been selected to alternately inflate and deflate the patient's lungs through said airway apparatus, to alternately inflate and deflate said vest bladder, and to alternately inflate and deflate said abdominal restraint bladder in substantial synchronism with each other at a predetermined CPR rate; and, wherein said control means is operative when said circulatory assistance mode has been selected to alternately inflate and deflate the patient's lungs through said airway apparatus at said ventilation rate, and to alternately inflate and deflate said vest bladder and said abdominal restraint bladder in substantial synchrouism with each other at a circulatory assistance rate related to the measured heart rate of the patient.

30. An apparatus as recited in claim 1, wherein said vest comprises: a first sheet composed of a flexible, air-impermeable, nonextensible and washable material, said first sheet having a width greater than the circumference of a patient's body in the region of the thorax and having a height generally corresponding to the height of the thorax; a second sheet composed of a flexible, air-impermeable and washable material, said second sheet having a width and a height generally corresponding to the width and height of the thorax, the periphery of said second sheet being sealed to said first sheet so as to define said inflatable bladder between said first sheet and said second sheet; a fluid connector secured to said first sheet and located so as to provide a fluid flow path to and from said inflatable bladder of said vest; and, means affixed to said first sheet for securing said vest about the patient's body; and wherein said control means includes means coupled to said fluid connector so that said control means is in fluid communication with said inflatable bladder of said vest.

31. An apparatus as recited in claim 1, wherein said abdominal restraint comprises: a first sheet composed of a flexible, air-impermeable, nonextensible and washable material, said first sheet having a width greater than the circumference of a patient's body in the region immediately below the thorax and having a height generally corresponding to the height of the abdomen; a second sheet composed of a flexible, air-impermeable and washable material, said second sheet having a width and a height generally corresponding to the width and height of the abdomen, the periphery of said second sheet being sealed to said first sheet so as to define said inflatable bladder of said abdominal restraint between said first sheet and said second sheet; a fluid connector secured to said first sheet and located so as to provide a fluid flow path to and from said inflatable bladder of said abdominal restraint; and, means affixed to said first sheet for securing said abdominal restraint about the patient's body; and, wherein said control means includes means coupled to said fluid connector so that said control means is in fluid communication with said inflatable bladder of said abdominal restraint.

32. An apparatus for assisting and reproducing the pulmonary and cardiac functions of a patient, said apparatus comprising:
   an airway apparatus constructed so as to be placed during use in proximity to the patient's airway to provide fluid communication with the patient's lungs;
   a vest constructed so as to be secured during use about the portion of the patient's body in the region of the thorax, said vest including an inflatable bladder that overlies the patient's chest;
   an abdominal restraint constructed so as to be secured during use about the portion of the patient's body immediately below the thorax, said abdominal restraint including an inflatable bladder that overlies the patient's abdomen; and,
   control means that is in fluid communication with said airway apparatus, said vest bladder, and said abdominal restraint bladder, and with a source of gas at a positive pressure above atmospheric pressure and a source of gas as substantially atmospheric pressure, said control means including:
   airway pneumatic control means in fluid communication with said airway apparatus and responsive to respective first and second states in an airway control signal to respectively inflate the patient's lungs by coupling gas obtained from said source of gas at a positive pressure to said airway apparatus and deflate the patient's lungs by coupling said airway apparatus to said source of gas at substantially atmospheric pressure;

vest pneumatic control means in fluid communication with said vest bladder and responsive to respective first and second states in a vest control signal to respectively inflate said vest bladder by coupling gas obtained from said source of gas at a positive pressure to said vest bladder and deflate said vest bladder by coupling said vest bladder to said source of gas at substantially atmospheric pressure;

abdominal restraint pneumatic control means in fluid communication with said abdominal restraint bladder and responsive to first and second states in an abdominal restraint control signal to respectively inflate said abdominal restraint bladder by coupling gas obtained from said source of gas at a positive pressure to said abdominal restraint bladder and deflate said abdominal restraint bladder by coupling said abdominal restraint bladder to said source of gas at substantially atmospheric pressure; and, electronic control means supplying said airway control signal, said vest control signal, and said abdominal restraint control signal to said airway pneumatic control means, said vest pneumatic control means, and said abdominal restraint pneumatic control means, respectively, said electronic control means including means for measuring the heart rate of the patient and being operative to alternate said first and second states in said airway control signal at a predetermined ventilation rate, whereby the patient's lungs are alternately inflated and deflated at said predetermined ventilation rate, and to alternate said first and second states in each of said vest and abdominal restraint control signals at a circulatory assistance rate related to the measured heart rate of the patient, whereby said vest bladder and said abdominal restraint bladder are each inflated and deflated at said circulatory assistance rate.

33. An apparatus as recited in claim 32, wherein said electronic control means includes means for selectively adjusting said predetermined ventilation rate.

34. An apparatus as recited in claim 32, wherein said electronic control means includes means for selectively adjusting the duty-cycle of said alternate first and second states in said airway control signal.

35. An apparatus as recited in claim 32, wherein said electronic control means includes: means for detecting successive R-waves in an ECG signal obtained from the patient; means for determining an average R—R interval between said successive detected R-waves; and, means for initiating alternate first and second states in each of said vest and abdominal restraint control signals in response to a detected R-wave and at respective times subsequent to said detected R-wave that are related to said average R—R interval.

36. An apparatus as recited in claim 35, wherein said electronic control means is operative to initiate said alternate first and second states in each of said vest and abdominal restraint control signals in response to each said detected R-wave.

37. An apparatus as recited in claim 35, wherein said electronic control means is operative to initiate said alternate first and second states in each of said vest and abdominal restraint control signals in response to a predetermined number of successive detected R-waves.

38. An apparatus as recited in claim 35, wherein said electronic control means is operative to initiate said alternate first and second states in each of said vest and abdominal restraint control signals at the elapse of said average R—R interval from said detected R-wave.

39. An apparatus as recited in claim 35, wherein said electronic control means is operative to initiate said alternate first and second states in each of said vest and abdominal restraint control signals at a predetermined time before the elapse of said average R—R interval from said detected R-wave.

40. An apparatus as recited in claim 39, wherein said electronic control means includes means for selectively adjusting said predetermined time.

41. An apparatus as recited in claim 35, wherein said electronic control means includes means for selectively adjusting the duty-cycle of said alternate first and second states in said vest control signal.

42. An apparatus as recited in claim 35, wherein said electronic control means includes means for selectively adjusting the duty-cycle of said alternate first and second states in said abdominal restraint control signal.

* * * * *

UNITED STATES PATENT AND TRADEMARK OFFICE
CERTIFICATE OF CORRECTION

PATENT NO. : 4,424,806

DATED : January 10, 1984

INVENTOR(S) : Bill H. Newman et al.

It is certified that error appears in the above-identified patent and that said Letters Patent is hereby corrected as shown below:

| | |
|---|---|
| Column 3, line 6: | "a" should be --an-- |
| Column 15, line 64: | "236" should be --226-- |
| Column 18, line 31: | "a" should be --an-- |
| Column 20, line 22: | "claim 1" should be --claim 9-- |
| line 65: | "volumn" should be --volume-- |
| line 68: | "volumn" should be --volume-- |
| Column 21, line 66: | "synchrouism" should be --synchronism-- |

Signed and Sealed this

Eighth Day of May 1984

[SEAL]

Attest:

GERALD J. MOSSINGHOFF

Attesting Officer

Commissioner of Patents and Trademarks